(12) United States Patent
Slamon et al.

(10) Patent No.: US 6,696,271 B2
(45) Date of Patent: Feb. 24, 2004

(54) FROZEN TISSUE MICROARRAY TECHNOLOGY FOR ANALYSIS OF RNA, DNA, AND PROTEINS

(75) Inventors: Dennis J. Slamon, Woodland Hills, CA (US); Marlena Schoenberg Fejzo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 86 days.

(21) Appl. No.: 09/935,507

(22) Filed: Aug. 23, 2001

(65) Prior Publication Data

US 2003/0040035 A1 Feb. 27, 2003

(51) Int. Cl.$^7$ .......................... G01N 33/48; C12N 15/74
(52) U.S. Cl. ........................................ 435/40.5; 435/325
(58) Field of Search ................................ 435/40.5, 325

(56) References Cited

U.S. PATENT DOCUMENTS

| | | | |
|---|---|---|---|
| 6,103,518 A | 8/2000 | Leighton | |
| 6,251,601 B1 | 6/2001 | Bao et al. | |
| 6,258,541 B1 | 7/2001 | Chapkin et al. | |
| 6,335,163 B1 | * 1/2002 | Sharon | |

OTHER PUBLICATIONS

Moch, H. et al., "Identification of Potential Prognostic Parameters for Renal Cell Carcinoma by Tissue Microarray Analysis and cDNA Microarray Screening", Verhandlungen der Deutschen Gesellschaft fur Pathologie, vol. 83, 1999, pp. 225–232.
Penault–Llorca, F. et al., "Optimization of Immunohistochemical Detection of ERBB2 in Human Breast Cancer: Impact of Fixation", Journal of Pathology, vol. 173, No. 1, May 1994, pp. 65–75.
Richter, J. et al., "High–Throughput Tissue Microarray Analysis of Cyclin E Gene Amplification and Overexpression in Urinary Bladder Cancer", American Journal of Pathology, vol. 157, No. 3, Sep. 2000, pp. 787–794.
Bowen, C. et al., "Loss of NKX3.1 Expression in Human Prostate Cancer Correlates with Tumor Progression", Cancer Research, vol. 60, No. 21, Nov. 1, 2000, pp. 6111–6115.
Schrami, P. et al., "Tissue Microarrays for Gene Amplification Surveys in many Different Tumor Types", Clinical Cancer Research, vol. 5, No. 8, Aug. 1999, pp. 1966–1975.
Slamon, D.J. et al., "Studies of the HER–2/neu Proto–oncogene in Human Breast and Ovarian Cancer", Science, vol. 244, May 12, 1999, pp. 707–712.
Specht, K. et al., "Quantitative Gene Expression Analysis in Microdissected Archival Formalin–Fixed and Paraffin–Embedded Tumor Tissue", American Journal of Pathology, vol. 158, No. 2, Feb. 2001, pp. 419–429.
Traweek, S.T. et al., "The Human Hematopoietic Progenitor Cell Antigen (CD34) in Vascular Neoplasia", Anatomic Pathology, vol. 96, No. 1, 1991, pp. 25–31.
Werner, M. et al., "Effect of Formalin Tissue Fixation and Processing on Immunohistochemistry", The American Journal of Surgical Pathology, vol. 24, No. 7, Jul. 2000, pp. 1016–1019.
Barlund, M. et al., "Multiple Genes at 17q23 Undergo Amplification and Overexpression in Breast Cancer", Cancer Research, vol. 60, No. 19, Oct. 1, 2000, pp. 5340–5344.
Battifora, H. et al, "The Influence of Protease Digestion and Duration of Fixation on the Immunostaining of Keratins. A Comparison of Formalin and Ethanol Fixation", The Journal of Histochemistry and Cytochemistry, vol. 34, No. 8, Aug. 1986, pp. 1095–1100.
Bubendorf, L. et al., "Survey of Gene Amplifications during Prostate Cancer Progression by High–Throughput Fluorescence in Situ Hybridization on Tissue Microarrays", vol. 59, No. 4, Feb. 15, 1999, pp. 803–806.
Bubendorf, L. et al., "Hormone Therapy Failure in Human Prostate Cancer: Analysis by Complementary DNA and Tissue Microarrays", Journal of the National Cancer Institute, vol. 91, No. 20, Oct. 20, 1999, pp. 1758–1764.
Barlund, M. et al, "Detecting Activation of Ribosomal Protein S6 Kinase by Complementary DNA and Tissue Microarray Analysis", Journal of the National Cancer Institute, vol. 92, No. 15, Aug. 2, 2000, pp. 1252–1259.
Goldsworthy, S.M. et al., "Effects of Fixation on RNA Extraction and Amplification from Laser Capture Microdissected Tissue", Molecular Carcinogenesis, vol. 25, No. 1, May 1999, pp. 86–91.
Kononen, J. et al., "Tissue microarrays for high–throughput molecular profiling of tumor specimens", Nature Medicine, vol. 4, No. 7, Jul. 1998, pp. 844–847.
Masuda, N. et al., "Analysis of chemical modification of RNA from formalin–fixed samples and optimization of molecular biology applications for such samples", Nucleic Acids Research, vol. 27, No. 22, Nov. 15, 1999, pp. 4436–4443.
Moch, H. et al., "High–Throughput Tissue Microarray Analysis to Evaluate Genes Uncovered by cDNA Microarray Screening in Renal Cell Carcinoma", American Journal of Pathology, vol. 154, No. 4, Apr. 1999, pp. 981–986.

* cited by examiner

Primary Examiner—Christopher R. Tate
Assistant Examiner—Randall Winston
(74) Attorney, Agent, or Firm—Gates & Cooper LLP

(57) ABSTRACT

The invention disclosed herein improves upon existing tissue microarray technology by using frozen tissues embedded in tissue embedding compound as donor samples and arraying the specimens into a recipient block comprising tissue embedding compound. Tissue is not fixed prior to embedding, and sections from the array are evaluated without fixation or post-fixed according to the appropriate methodology used to analyze a specific gene at the DNA, RNA, and/or protein levels. Unlike paraffin tissue arrays which can be problematic for immunohistochemistry and for RNA in situ hybridization analyses, the disclosed methods allow optimal evaluation by each technique and uniform fixation across the array panel. The disclosed arrays work well for DNA, RNA, and protein analyses, and have significant qualitative and quantitative advantages over existing methods.

6 Claims, 4 Drawing Sheets

(4 of 4 Drawing Sheet(s) Filed in Color)

FIGURE 1A-D
A.
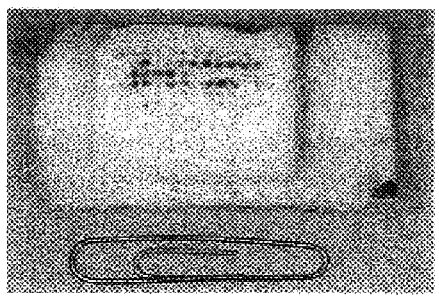
B.
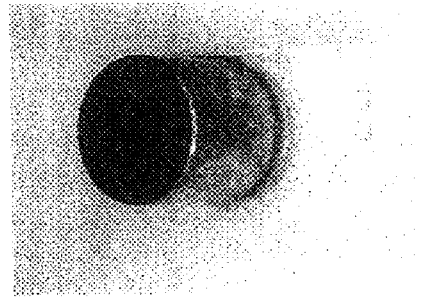
C.
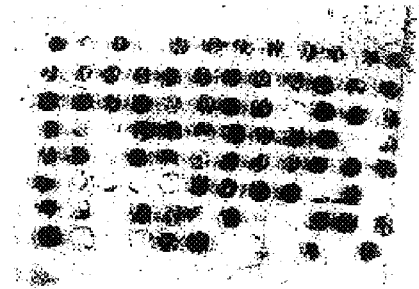
D.
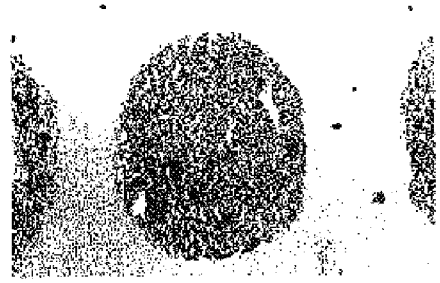

FIGURE 2A-B

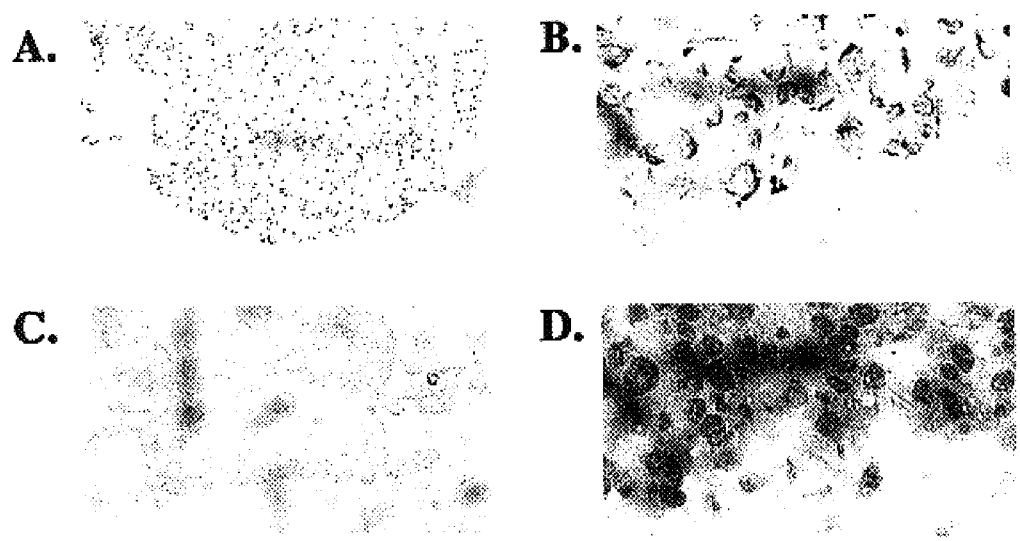
FIGURE 4A-D

FROZEN TISSUE MICROARRAY TECHNOLOGY FOR ANALYSIS OF RNA, DNA, AND PROTEINS

FIELD OF THE INVENTION

This invention relates generally to tissue microarray technology. Microarray technology allows the rapid analysis of hundreds to thousands of genes, mRNAs, proteins, and tissue samples in expedited experimental approaches and is used to identify and characterize genes and markers involved in a variety of human pathologies.

BACKGROUND OF THE INVENTION

Recently developed high density tissue microarray technology involves arraying up to thousands of cylindrical tissue cores from individual tumors on a tissue microarray (see, e.g. Kononen et al. Nat Med. 1998 July ;4(7):844–7). More than two hundred serial sections can then be made from an individual microarray block and used for analysis of DNA, RNA, and/or proteins on a single glass slide. The technology is useful in that it allows rapid analysis of a large number of samples so that the statistical relevance of new markers can be determined in a single experiment. In addition, altered expression levels can be correlated to amplification or deletion events in specific tumor samples using serial sections, allowing simultaneous determination of gene copy number and expression analysis of candidate pathogenic genes and suppressor genes. Arrays have been made containing numerous tumor types (see, e.g. Schraml et al. Clin Cancer Res. 1999 August ;5(8):1966–75) as well as multiple stages and grades within individual tumor types (see, e.g. Moch et al. Am J Pathol. 1999 April ;154(4):981–6; Bubendorf et al. Cancer Res. Feb. 15, 1999 (4):803–6 and Bubendorf et al. J Natl Cancer Inst. Oct. 20, 1999 ;91(20):1758–64). This new technology has already proven useful for rapidly characterizing the prevalence and prognostic significance of differentially expressed genes identified using cDNA array technology (see, e.g. Bubendorf et al. J Natl Cancer Inst. Oct. 20, 1999;91(20):1758–64; Moch et al. Verh Dtsch Ges Pathol. 1999;83:225–32. German and Barlund et al. J Natl Cancer Inst. Aug. 20, 2000 ;92(15):1252–9) as well as genes involved in cancer development and progression (see, e.g. Bubendorf et al. Cancer Res. Feb. 15, 1999;59(4):803–6 and Bubendorf et al. J Natl Cancer Inst. Oct. 20, 1999;91(20):1758–64). Tissue microarrays have also been useful in identifying genes that are targets of chromosomal amplification (see, e.g. Barlund et al. Cancer Res. Oct. 1, 2000; 60(19):5340–4 and Richter et al. Am J Pathol. 2000 September ;157(3):787–94) as well as to study the expression patterns of putative tumor suppressor genes (see, e.g. Bowen et al. Cancer Res. Nov. 1, 2000;60(21):6111–5).

A variety of technical problems exist with the current methodology, however, relating to the fact that the arrayed samples have to be pre-fixed and embedded in paraffin. The quality of the studies performed on sections from tissue array technology may be limited by the fixation methods used on the original sample. Buffered formalin solutions (and related compounds) are among the most widely used tissue fixatives. These chemicals fix the tissue by acting as progressive cross linkers between proteins and nucleic acids, by introducing modifications in RNA (adding mono-methyl groups to its bases), and by producing coordinate bonds for calcium ions; these processes can damage RNA and alter target antigenic structure by blocking or damaging antibody binding sites (see, e.g. Masuda et al. Nucleic Acids Res. Nov. 15, 1999;27(22):4436–43 and Werner et al. Am J Surg Pathol. 2000 July;24(7):1016–9. Review). Formalin fixation-induced alterations can make in-situ analysis of DNA, RNA, and proteins suboptimal and variations in the duration of fixation can effect the quality and reproducibility of results (see, e.g. Kononen et al. Nat Med. 1998 July;4(7):844–7; Werner et al. Am J Surg Pathol. 2000 July;24(7):1016–9, Review and Specht et al. Am J Pathol. 2001 February;158(2):419–429). Artisans attempt to overcome fixation problems for FISH by uniformly pre-fixing tissues in cold ethanol and embedding in paraffin (see, e.g. Kononen et al. Nat Med. 1998 July;4(7):844–7), but this approach is not optimal for array analysis of some proteins or for RNA using in situ hybridization. Paraffin embedding of ethanol-fixed tissue does not prevent RNA degradation (see, e.g. Goldsworthy et al. Mol Carcinog. 1999 June;25(2):86–91). In addition, while ethanol fixation of tissue and subsequent paraffin embedding circumvents formalin fixation-related problems introduced by crosslinking, there are still problems relating to the embedding, and/or deparaffinization processes such as temperature-induced antigenic alterations introduced during the embedding process (see, e.g. Werner et al. Am J Surg Pathol. 2000 July;24(7):1016–9, Review; Battifora et al. J Histochem Cytochem. 1986 August;34(8):1095–100 and Penault-Llorca et al. J Pathol. 1994 May;173(1):65–75).

Consequently there is a need in the art to identify additional methods that allow for the optimal preservation of biological molecules such as polypeptides and polynucleotides to be analyzed in such arrays. The present invention meets this need in the art by providing methods that circumvent problems associated with traditional paraffin arrays.

SUMMARY OF THE PREFERRED EMBODIMENTS

The invention disclosed herein improves upon existing tissue microarray technology by arraying the specimens into a recipient block comprising tissue embedding compound. Tissue is not fixed prior to embedding, and sections from the array are evaluated without fixation or post-fixed according to the appropriate methodology used to analyze a specific gene at the DNA, RNA, and/or protein levels.

The invention disclosed herein includes a number of embodiments. A typical embodiment of the invention is method of preparing a tissue microarray by embedding a non-fixed biological sample in the tissue microarray block, wherein the tissue microarray block comprises frozen tissue embedding compound. A related embodiment of the invention includes a method of preparing a tissue microarray comprising the steps of: preparing a tissue microarray block for receipt of a biological sample, wherein the tissue microarray block comprises frozen tissue embedding compound; removing a core sample of a biological sample from a frozen donor block comprising tissue embedding compound; and then placing the core sample of the biological sample into an array within the tissue microarray block. Yet another embodiment of the invention is a method of preparing a biological sample for microarray analysis comprising the steps of: preparing a tissue microarray block for receipt of a biological sample; freezing the biological sample in tissue embedding compound; removing a core sample of the biological sample from the frozen tissue embedding compound; and then placing the core sample of the biological sample into an array within the tissue microarray block, wherein the tissue microarray block comprises frozen tissue embedding compound.

A number of variations on these methods are disclosed herein. In preferred embodiments for example, the biological sample is prepared for placement into the tissue microarray block by removing a core sample of frozen biological material from a donor block comprising frozen tissue embedding compound. Preferably, the biological material is removed from the frozen tissue embedding compound with a coring means having a temperature of less than about 4 degrees centigrade. In yet another embodiment of the invention, a slice of an about 4 µm section of the frozen tissue microarray block comprising a portion of the biological sample is removed for subsequent analysis. In such embodiments of the invention, the tissue can be fixed after being embedded in the frozen tissue embedding compound.

Another embodiment of the invention includes a process for preparing a biological sample for microarray analysis comprising embedding a non-fixed biological sample into an array within a block comprising frozen tissue embedding compound. A closely related embodiment includes a biological sample for microarray analysis prepared by this process. Embodiments of the invention also include compositions comprising an array of biological samples having at least one non-fixed biological sample embedded in a tissue microarray block, wherein the tissue microarray block comprises frozen tissue embedding compound.

The invention also provides article of manufacture or kit comprising one or more polypeptide and/or polynucleotide probes and a tissue embedding medium.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The file of this patent contains at least one drawing executed in color. Copies of this patent with color drawing (s) will be provided by the patent and Trademark Office upon request and payment of the necessary fee.

FIG. 1: Frozen Microarray Method and HE staining. A) A total of 96 1.0 mm samples from solid tumor mouse xenografts (derived from Calu-6, a human lung cancer cell line) spaced 1.0 mm apart are embedded in an O.C.T. block mounted on a plastic cassette as described in the Materials and Methods. B) After the array is completed, a cylinder is mounted with O.C.T. to the back of the array which readily fits into the Hacker OTF cryostat for sectioning. C) A 4 micron section of the block shown in 1A is HE-stained to show overall integrity and spacing, and D) 4×magnification of the same section shows level of tissue and cell morphology maintained in the OCT array.

FIG. 2: Non-radioactive RNA in situ hybridization. Non-radioactive RNA in situ hybridization with digoxigenin-labeled actin on frozen tissue microarray Calu-6 mouse xenograft sample at A) 20×magnification shows mRNA expression levels can be assessed using this technology. B) Negative control on a consecutive 4 micron section at 20×magnification shows no signal.

FIG. 4: Immunohistochemistry. Antibody staining for the EGF receptor on frozen array sample MDA-MB-231 (human breast cancer cell line known to express EGF receptor) shows at A) 4×magnification that staining is relatively uniform and specific across the sample, and B) at 40X magnification shows expected membrane-specific staining when compared to C) no background staining on serial section with secondary antibody staining only, and D) HE staining of the same sample from a serial section of the array.

DETAILED DESCRIPTION OF THE PREFERRED EMBODIMENTS

Figure 3:
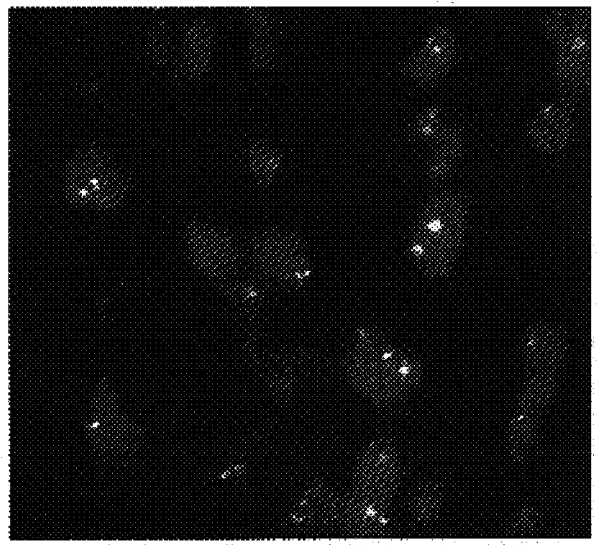
FIG. 3: Fluorescent in Situ Hybridization (FISH). FISH on Calu-6 mouse xenograft tissue microarray 4 micron section shown in FIG. 1 shows intense signals with a chromosome 8 centromere probe (Vysis). Signals are easily detected on DAPI-counterstained nuclei at 100× magnification with a triple-pass filter on a fluorescent microscope.

Unless otherwise defined, all terms of art, notations and other scientific terms or terminology used herein ate intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The term "biological sample" is used herein according to its broadest meaning and refers to the wide variety of biological materials that can be analyzed in tissue microarrays. Biological materials typically analyzed in tissue microarrays include tissues from specific organs such as brain, kidney, liver heart, bone, prostate and other tissues, as well as fluid materials such as serum, urine, semen etc. Such materials also include in vivo and in vitro cellular materials such as cancer cells and cell lines. The macromolecules analyzed in these materials typically include polypeptides such as proteins as well as polynucleotides such as RNA and DNA.

The term "tissue embedding compound" as used herein refers to art accepted compounds artisans utilize to rapidly freeze biological materials for histopathological analysis, for example the medium sold by Tissue Tek® under the name "O.C.T. (optimal cutting temperature) compound™" (product code 4583) and the medium sold by Instrumedics® Inc. under the name "Cryo-Gel™" (Cat#ICG-12). Tissue embedding compounds are characterized as being generally non-reactive with biological materials and having a high degree of viscosity due to the presence of viscosity generating substances such as polyvinyl alcohol and polyethylene glycol (see, e.g. O.C.T. compound which is composed of 10.24% polyvinyl alcohol, 4.26% polyethylene glycol and 85.50% non-reactive ingredients). This definition excludes paraffin compounds typically used in tissue microarrays.

The terms "fixing" and "fixed" are used according to their art accepted meaning and refer to the chemical treatment (typically cross-linking) of biological materials such as proteins and nucleic acids that can be accomplished by the wide variety of fixation protocols known in the art (see, e.g., Current Protocols In Molecular Biology, Volume 2, Unit 14, Frederick M. Ausubul et al. eds., 1995). The term "non-fixed" refers to biological materials that have not been chemically modified or treated (e.g. with reagents such as formalin and ethanol) according to such protocols.

As noted above, microarray technology allows for the rapid analysis of hundreds to thousands of genes, proteins, and other macromolecules in expedited experimental approaches (see, e.g. Kononen et al. Nat Med. 1998 July;4 (7):844–7). This relatively new technology has already shown potential in rapidly identifying and characterizing genes and markers involved in the pathogenesis of human cancers (see, e.g. Schraml et al. Clin Cancer Res. 1999 August;5(8):1966–75; Moch et al. Am J Pathol. 1999 April;154(4):981–6; Bubendorf et al. Cancer Res. Feb. 15, 1999;59(4):803–6; Bubendorf et al. J Natl Cancer Inst. Oct. 20, 1999;91(20):1758–64; Moch et al. Verh Dtsch Ges Pathol. 1999;83:225–32. German and Barlund et al. J Natl Cancer Inst. Aug. 2, 2000;92(15):1252–9; Barlund et al. Cancer Res. Oct. 1, 2000; 60(19):5340–4; Richter et al. Am J Pathol. 2000 September;157(3):787–94 and Bowen et al. Cancer Res. Nov. 1, 2000 ;60(21):6111–5). To date, human malignant tissue microarrays are most commonly constructed from archival paraffin tissue blocks. The paraffin-based technology may not be optimal for studying RNA, DNA, and proteins simultaneously on a single array because FISH, RNA in situ, and immunohistochemistry all have different optimal fixation conditions.

The tissue microarrays described herein are made by modifying the methods used with traditional formalin-fixed paraffin-embedded biological samples. In such conventional methods, the sampling of the original tissues for arraying is performed from morphologically representative regions of regular formalin-fixed paraffin-embedded tumor blocks. Core tissue biopsies (diameter 0.6 mm, height 3–4 mm) are taken from individual "donor" blocks and arrayed into a new "recipient" paraffin block (45×20 mm) using a tissue microarraying instrument (Beecher Instruments Inc.). Typically artisans prefer cylinders ranging from about 0.6 to about 2.0 mm, which convey some histological information, yet allow up to one thousand specimens to be arrayed in each block with little damage to the original blocks. The donor block is manually positioned for sampling based on a visual alignment with the corresponding HE-stained section on a slide. The region of interest for punching in each tumor is carefully selected from the H&E stained slide. After the block construction is completed, about 4 to about 10 $\mu$m sections of the resulting tumor tissue microarray block are cut with a microtome. An adhesive-coated tape sectioning system (Instrumedics Inc.) can be used for assisting sectioning of the tumor array blocks. On average, two hundred sections can be cut from one tumor tissue microarray block. HE-staining for histology verification can be performed periodically such as every 50th section cut from the block. Tissue microarray slides can be evaluated either manually or utilizing a high-throughput digital imaging system. For brightfield image acquisition artisans typically utilize systems such as those produced by Carl Zeiss which ate based on high-resolution (4k×3k pixels) digital cameras.

Technical problems with the existing methodology are related to the fact that the arrayed samples have been pre-fixed and embedded in paraffin. One way to avoid these problems and ensure optimal preservation of antigens and nucleic acids is to use non-fixed (e.g. fresh frozen) tissue frozen at –70° C. (see, e.g. Slamon et al. Science. May 12, 1989;244(4905):707–12 and Battifora et al. Am J Clin Pathol. 1991). The methods disclosed herein overcome problems associated with paraffin arrays and demonstrate the feasibility of using frozen tissue for creating tumor tissue microarrays.

The invention disclosed herein is represented by a number of embodiments. A typical representative embodiment includes a method of preparing a tissue microarray comprising the steps of: preparing a tissue microarray block for receipt of a biological sample; and embedding a non-fixed biological sample in the tissue microarray block, wherein the tissue microarray block comprises frozen tissue embedding compound. Typically the tissue microarray block is prepared for receipt of a biological sample by positioning it to receive this sample from a sample dispensing means. In preferred embodiments of the invention, the biological sample is prepared for placement into the tissue microarray block by removing a core sample of frozen biological material from a donor block that also comprises frozen tissue embedding compound. While the donor and recipient blocks may comprise different compounds, in preferred embodiments they are both formed from tissue embedding compound. In highly preferred embodiments of the invention, the core sample of the biological material is removed from the frozen tissue embedding compound with a coring means having a temperature of less than about 4 degrees centigrade (and preferably less than about –20° centigrade). Modifications to these methods include slicing an about 4 $\mu$m section off of the frozen tissue microarray block; wherein the section comprises a portion of the biological sample. In certain embodiments of the invention, the tissue is fixed after being embedded in the frozen tissue embedding compound and sectioned from the block.

Preferred tissue embedding compounds include the medium sold by Tissue Tek® under the name "O.C.T. (optimal cutting temperature) compound™" (product code 4583) and the medium sold by Instrumedics® Inc. under the name "Cryo-Gel™" (Cat#ICG-12). These tissue embedding compounds function to rapidly freeze biological samples and typically comprise viscosity agents such as about 5% to about 20% polyvinyl alcohol and/or about 1% to about 10% polyethylene glycol. In preferred embodiments of the invention, the tissue embedding compound comprises about 10% polyvinyl alcohol and about 4% polyethylene glycol.

Other embodiments of the invention include a method of preparing a biological sample for microarray analysis by freezing the biological sample in tissue embedding compound, removing a core sample of the biological sample from the frozen tissue embedding compound, preparing a tissue microarray block for receipt of a biological sample and then placing the core sample of the biological sample into an array within the tissue microarray block, wherein the tissue microarray block comprises frozen tissue embedding compound. In preferred aspects of the invention, the core sample of the biological sample is removed from the frozen tissue embedding compound with a coring means having a temperature of about –50° C. degrees centigrade. Modifications to these methods include slicing an about 4 $\mu$m section off of the frozen tissue microarray block; wherein the section comprises a portion of the biological sample. In certain embodiments of the invention, the tissue is fixed after being embedded in the frozen tissue embedding compound.

Yet another embodiment of the invention includes a method of preparing a tissue microarray comprising the steps of preparing a tissue microarray block for receipt of a biological sample, wherein the tissue microarray block comprises frozen tissue embedding compound, removing a core sample of a biological sample from a frozen donor block comprising tissue embedding compound and then placing the core sample of the biological sample into an array within the tissue microarray block. In preferred aspects of the invention, the core sample of the biological sample is removed from the frozen tissue embedding compound with a coring means having a temperature of about −50° C. degrees centigrade. Modifications to these methods include slicing an about 4 μm section off of the frozen tissue microarray block; wherein the section comprises a portion of the biological sample. In certain embodiments of the invention, the tissue is fixed after being embedded in the frozen tissue embedding compound.

Yet another embodiment of the invention is a process for preparing a biological sample for microarray analysis comprising embedding a non-fixed biological sample into an array within a block comprising frozen tissue embedding compound. A closely related aspect of this embodiment is a biological sample for microarray analysis prepared by this process. A highly preferred embodiment of the invention is a composition comprising an array of biological samples comprising at least one non-fixed biological sample embedded in a tissue microarray block, wherein the tissue microarray block comprises frozen tissue embedding compound. Specific illustrations of the various embodiments of the invention discussed in the preceding paragraphs ate provided below.

As disclosed in Example 1, test arrays (40×0.6 mm diameter samples and 96×1.0 mm samples) using the methods disclosed herein were created. This example demonstrates how samples can be cored from frozen tissue samples (and cell lines) embedded in O.C.T. compound (or directly thawed for cell lines) and placed into a frozen O.C.T. recipient array block for sectioning and subsequent storage. The standard 0.6 mm microarray needles (Beecher Instruments, Silver Spring, Mich.), which are used for the paraffin-based microarrays, can core frozen tissue, but minimal pressure must be applied to prevent needle breakage. Typically, larger (1.0 mm) needles (Beecher Instruments, Silver Spring, Mich.) are far sturdier and preferred. Frozen tumor tissue and cell lines embedded in O.C.T. compound were successfully cored and placed into an O.C.T. compound recipient block. The array was constructed with≧1 mm space between punches. A≧1 mm space between punches is preferred because arraying samples more proximally may cause some cracking in the recipient array block. The frozen tissue array samples maintained adequate morphology as seen when sections as thin as 4 microns were cut and HE stained (FIGS. 1C and 1D). A tape transfer system (Instrumedics Inc.) facilitated maintaining the integrity of the samples (compare array in 1A to HE-stained slide made from section of 1A, shown in 1C). Similar results were obtained using a tape transfer system to section a human breast tumor array. The morphology and integrity of the human breast tumor array was comparable to the array shown in FIGS. 1C and 1D providing evidence that this technique will be successful when using fatty tissues that are generally difficult to section using standard methods (cryosectioning without the tape system).

In a typical test array, 96 samples (with 1 mm diameter) were easily fit in the array block with room to add more samples if needed (FIG. 1A). This sample size is equivalent to that seen in commercially available paraffin arrays. For example, currently paraffin arrays containing up to sixty individual tissue samples (with 2 mm diameter) and up to two hundred individual tissue samples (with 0.6 mm diameter) can be purchased from SuperBioChips Laboratories, Seoul, Korea, and Invitrogen Corp., San Diego, Calif., respectively. To fit more samples on the frozen array, a larger mold (e.g. a plastic cryomold or a metal paraffin mold) can be used, or a smaller needle can be used to fit more samples in the same space. The smaller needle biopsies have two considerations: (1) the smaller needles break more easily; and (2) there is less representation of the tumor the biopsy is derived from. One way to overcome problems with needle breakage problem is to let the frozen tissue thaw a little before biopsying the sample. In the methods disclosed herein, briefly thawing frozen tissue did not effect test RNA (actin) quality.

To demonstrate how the tumor tissue microarray can be used for analysis of RNA, non-radioactive RNA in situ hybridization was performed on the tissue microarray slide using a digoxigenin labeled actin RNA probe. As disclosed in Example 2, array slides were fixed for 10 minutes, 2 hours, or overnight in 4% paraformaldehyde to test whether shorter fixation times could be used for non-radioactive RNA in situ hybridization. Using actin as a probe, the studies demonstrated excellent preservation of intact RNA when the array section was fixed overnight in 4% paraformaldehyde (FIG. 2). Slides fixed for 10 minutes and 2 hours showed no signal suggesting shorter fixation times may result in ineffective fixation.

As disclosed in Example 3, methods employing a frozen tissue array are an excellent approach for FISH based experiments to analyze DNA (FIG. 3). To demonstrate this, FISH of a chromosome 8 centromere probe to the frozen tissue microarray was assayed to test whether the array could be used for in situ analysis of tumor DNAs. To determine which fixative works best for FISH to the frozen tissue microarray, array slides were fixed in either Carnoy's fixative or ethanol. A slightly stronger signal was observed when slides for FISH were pre-fixed with Carnoy's fixative as compared to ethanol fixation, but both worked well. Array slides were also pretreated with and without proteinase K to determine whether proteinase K treatment would have an effect on the quality of hybridization and signal intensity. The proteinase K treatment did not improve hybridization efficiency or signal intensity, as the probe penetrated the frozen tissue equally well under both conditions.

As disclosed in Example 4, immunohistochemical methods are easily performed with a frozen tissue array. To demonstrate this, immunohistochemistry on the tumor tissue microarray with antibodies for the EGF receptor (HER-1) and heregulin was performed. The EGF receptor staining is uniform across the sample (FIG. 4A) and gives the expected membrane-associated staining, as seen when comparing the EGF receptor-stained sample with a serial HE-stained section (FIG. 4B,D). There is no background staining using the secondary antibody alone (FIG. 4C). Similar results were obtained using the heregulin antibody except the staining showed the expected diffuse cytoplasmic signal. Antibodies to heregulin and the EGF receptor both result in cell-specific signals showing this methodology is useful for immunohistochemical based protein analyses as well.

The generation of a frozen tissue microarray comprising non-fixed tissues has a number of advantages over conventional practices. For example, such methods overcome problems associated with formalin fixation-induced alterations that effect the quality and reproducibility of in-situ analysis of DNA, RNA, and proteins (see, e.g. Iononen et al. Nat Med. 1998 July;4(7):844–7; Werner et al. Am J Surg Pathol. 2000 July;24(7):1016–9, Review and Specht et al. Am J Pathol. 2001 February;158(2):419–429). In addition, by fixing a biological sample after the tissue microarray is constructed, one optimizes the study of a specific macromolecule of interest by using the optimal fixing protocol(s) that depend on the specific characteristics of that molecule (e.g. DNA, RNA, or proteins). In this way, different molecules of interest from a single tissue microarray can be evaluated in parallel sections under optimal conditions (e.g. a first section fixed for the evaluation of polynucleotides and a second section from the same microarray fixed for the evaluation of polypeptides). Other benefits include the uniform fixation across the array panel that occurs when a biological sample is fixed after the tissue microarray is constructed (thereby decreasing signal variability that is associated with inconsistent fixing).

Frozen biological materials are typically difficult to manipulate without cracking or otherwise compromising the integrity of the frozen matrix in which they are embedded. Consequently, a skilled artisan would expect a frozen material to crack when exposed to the significant mechanical stresses associated with tissue microarray protocols. Such mechanical stresses include those associated with the coring of the microarray block (typically involving hundreds of punctures) as well as the stresses associated with cutting about 4 to about 10 μm sections of the microarray block prior to their analysis. Consequently it is surprising that tissue microarrays can in fact be generated using biological materials placed within a frozen matrix such as tissue embedding medium. Moreover, because it is not possible to predict how the freezing of a biological material in a specific medium and its subsequent manipulation and analysis in that medium will effect the histological data obtained in the context of a tissue microarray (e.g. the possibility that the frozen material will break apart when manipulated in this manner) the results described in Examples 2–4 are unexpected. In addition, the finding that tissue microarrays which incorporate non-fixed biological materials produce results comparable to which incorporate fixed biological materials is unexpected in view of art which teaches the advantages of fixing biological materials in microarray protocols.

As demonstrated herein, frozen tissue microarrays provide excellent target material for the study of DNA, RNA, and proteins by fixing each array slide in a manner specific to the corresponding technique used. While there is some distortion of cell morphology and tissue architecture compared to formalin fixed paraffin embedded arrays, this is commonly seen when comparing frozen sections to paraffin sections. In addition, skilled artisans will understand the need to modify traditional methods when working with a frozen medium, for example the fact that the tissue embedding compound may bend and crack when samples are placed at less than 1 mm apart.

A significant advantage of the frozen microarray approach stems from the fact that certain antibodies, DNA, and RNA probes do not perform optimally in pre-fixed paraffin embedded tissues. These reagents work very well using the technology presented here. Another advantage of the frozen tissue microarrays is that those procedures requiring fixation can be conducted in samples fixed in an identical manner. Therefore, a higher proportion of the arrayed samples may be included in the final analysis than with the paraffin embedded tumor microarrays. As demonstrated herein, frozen tumor tissue microarrays provide an excellent way to store and analyze tumor samples and may prove useful for identifying novel molecular targets for diagnosis, prognosis, and therapy of cancer, as well as for validation of cDNA microarray studies. By allowing simultaneous analysis of uniformly and optimally fixed DNA, RNA, and proteins from hundreds of tumor samples, this technology facilitates advances in the understanding of tumor pathobiology.

As is known in the art, one can utilize a variety of techniques known in this art to enhance and/or improve upon microarray methods. In particular, one can employ and or modify methods from traditional paraffin arrays to be used with the non-fixed frozen tissue arrays disclosed herein (see, e.g. U.S. Pat. Nos. 6,103,518, 6,258,541 and 6,251,601). In addition, variations on analyses include the variety of means used in the art to optimize the interpretation of data such as such as statistical sampling. For example skilled artisans can overcome challenges associated with sampling error, by taking multiple biopsies from each sample. A recent study of immunohistochemistry on paraffin arrays has shown that double sampling of 0.6 mm diameter punches of tumors leads to representation of the original tumor in at least 95% of the tumors on the array (see, e.g. Camp et al. Lab Invest 2000 December;80(12):1943–9). Double punching may also improve representation using the larger needles as well. Separate recipient arrays can be made representing duplicate samples so that total sample number doesn't have to be limited by double-punching.

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a molecule of interest. Where the method utilizes nucleic acid hybridization to detect the target nucleic acid, the kit can also have containers containing nucleotide(s) for identification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including mediums and package inserts with instructions for use. A label can be present on the container to indicate that the composition is used for a specific application, and can also indicate directions for tissue use, such as those described above. Directions and or other information can also be included on an insert which is included with the kit A variety of modifications and improvements to the present invention will be apparent to those skilled in the art. While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein. All patent and patent application and literature references cited in the present specification are hereby incorporated by reference in their entirety.

EXAMPLES

Example 1

Frozen Array Construction

A human lung cancer cell line CALU-6 grown as a mouse xenograft and human breast cancer cells MDA-MB-231 grown in vitro and pelleted were frozen and embedded in O.C.T. compound embedding medium (Miles Inc. Diagnostic Division, Elkhart, Ind.) to test whether arrays could be cored and collected in this medium. Methodology was as published previously (1), except that tissue biopsies (diameter 0.6 and 1.0 mm; height 3–4 mm) were punched from tumors in O.C.T. and placed directly into an O.C.T. array block using a tissue microarrayer (Beecher Instruments, Silver Spring, Md., USA).

The recipient O.C.T. array block was made by filling a Tissue-Tek standard cryomold (Miles Inc., Elkhart Ind.) with O.C.T. and mounting the O.C.T. filled mold to the base of a plastic biopsy cassette (Simport Histosette II Biopsy Cassette from Fisher Scientific with lid removed), see FIG. 1A. The recipient O.C.T. block has the same size base as the paraffin recipient block that the tissue microarrayer was made to accommodate, and therefore it was easily mounted in the tissue microarrayer (Beecher Instruments). The recipient block must be surrounded with dry ice to prevent melting. The same needle (0.6 or 1.0 mm Beecher Instruments, Silver Spring, Mich., USA) was used for both coring the recipient array block and collecting the core biopsy rather than switching to a larger needle for the biopsies. The tissue in the needle was kept frozen by holding the needle against a piece of dry ice before and after punching the tissue and while dispensing the tissue core into the recipient block. Punching and coring were done slowly with minimal pressure to prevent needle breakage. The recipient array was kept frozen by placing a piece of dry ice on its upper surface at all times except when punching and filling holes. A space of one millimeter was left between each 0.6 or 1.0 mm punch.

Multiple arrays were created to demonstrate the feasibility of this method. One array contained 40 samples (0.6 mm in diameter). This array consisted of 20 samples of a cell line (MDA-MB-231) frozen in O.C.T. (frozen cells quick-thawed and pipetted into a hole in the recipient O.C.T. block also work), and 20 biopsies of a solid tumor frozen in O.C.T. (Calu6 mouse xenografts) cored and placed in the recipient O.C.T. block. The second array contained 96 biopsies (1.0 mm in diameter) of solid tumors frozen in O.C.T. (Calu6 mouse xenografts), shown in FIG. 1. After the frozen tissue arrays were completed, a mounting cylinder (Hacker Instruments Inc., Fairfield, N.J., USA) was fixed with O.C.T. medium to the back of the array (FIGS. 1A and 1B). 4–10 micron sections of the whole block were cut from the array block using a cryostat microtome (Hacker Instruments Inc.) and the Basic Cryojane Tape Transfer System and slides (Instrumedics Inc., Hackensack N.J.). The remaining tissue array was stored at −70° C. Slides were HE-stained to assess the morphological integrity of the tissue microarray (FIGS. 1C and 1D).

A tape transfer system (Instrumedics, Inc.) facilitates the preservation of the morphology and integrity of the array. As shown in FIGS. 1C and 1D, HE staining was done on sections using the tape system and the frozen tissue array samples maintains adequate morphology as seen when sections as thin as 4 micron were cut and HE stained (FIGS. 1C and 1D). The tape transfer system (Instrumedics Inc.) facilitates the maintenance of the integrity of the samples (compare array in 1A to HE-stained slide made from section of 1A, shown in 1C). Using the tape transfer system when sectioning arrays, there was no problem sectioning a cell line (MDA-MB-231) or solid tumors (mouse xenografts derived from Calu6). Additionally, there was no problem sectioning frozen breast tissue array. The morphology and integrity of the human breast tumor array was comparable to the array shown in figure 1C and 1D providing evidence that this technique is successful with tissues that are generally difficult to section using standard methods.

Example 2

Non Radioactive RNA in situ Hybridization Methods Employing Frozen Arrays

Nonradioactive RNA in situ hybridization was performed as published previously for frozen sections (see, e.g. Hogan et al. Manipulating the Mouse Embryo: A Laboratory Manual. New York: Cold Spring Harbor Laboratory Press (1994). Briefly, tissue array sections used for RNA in situ hybridization were fixed in 4% paraformaldehyde in phosphate buffered saline (PBS) for either 10 minutes, 2 hours, or overnight at 4 C. Slides were rinsed 3 times in PBS for 5 minutes each and drained. Sections were covered with a prehybridization buffer (50% deionized formamide, 5×SSC, 5×Denhardt's, 750 µg/ml torula RNA) and placed in a humid chamber at room temperature for 2 hours. Hybridization was performed by adding 0.5 micrograms of digoxigenenin-labeled actin RNA probe (Boehringer Mannheim, Germany) to 10 ml of prehybridization solution in a 5-slide mailer. Tissue nucleic acid was denatured at 85 C for 10 minutes and cooled on ice. The RNA probe was omitted as a negative control to determine background due to detection reagents. Slides were hybridized overnight at 70 C, then washed in 5×SSC at 70 C for 5 minutes and in 0.2×SSC at 70 C for 60 minutes. Sections were next washed for 5 minutes in buffer B1(0.1 M maleic acid, 0.15 M NaCl) and placed in a humid chamber with blocking solution (1% Blocking agent Boehringer-Mannheim, Germany) for 1 hour at room temperature. Slides were then drained and incubated at room temperature for 1 hour with a 1:2000 dilution of AP conjugated alpha-digoxigenin antibody (Roche Diagnostics GmbH, Mannheim, Germany) in B2. The antibody was drained and slides were rinsed in B1 twice for 20 minutes each. Slides were next washed in B3 (100 mM Tris pH9.5, 100 mM NaCl, 5 mM MgCl2) for 5 minutes. Slides were then drained but not dried and covered with BM Purple substrate (Boehringer Mannheim GmbH, Germany) overnight. Signal was post-fixed in 4% paraformaldehyde in PBS, and the signal visualized using standard light microscopy.

Typical results of such an assay are shown in FIG. 2.

Example 3

Fluorescent in situ Hybridization Methods Employing Frozen Arrays

Frozen tissue microarray sections were fixed in Carnoy's fixative or 95% ethanol for 10 minutes. Slides were pre-treated in 2×SSC at 37 C for 30 minutes, dehydrated, denatured in 70% formamide/2×SSC for 5 minutes at 72 C, and dehydrated again. Slides were then treated either with or without 0.4 ug/mil proteinase K (Sigma, St. Louis, Mo., USA) at 37 C for 30 minutes. A spectrum orange chromosome 8 probe (Vysis Inc., Downer's Grove, Ill.) was prepared according to the manufacturer's instructions, denatured for 7 minutes at 72 C, and hybridized to the array slides overnight at 37 C in a humid chamber. Slides were washed (50% formanide/ 2×SSC 44 C, 15 minutes; 2×SSC, 8 minutes) and counterstained with DAPI (Vysis, Downersgrove, Ill., USA). Slides were visualized using standard fluorescent microscopy and photographed with Ektachrome 400 ASA slide film (Eastman Kodak, Rochester, N.Y., USA).

Typical results of such an assay are shown in FIG. 3.

Example 4

Immunohistochemical Methods Employing Frozen Arrays

Array slides for immunohistochemistry were prepared by sectioning of the block as described above, then fixed in cold 100% methanol for 15 minutes. Sections were rinsed in PBS, quenched in 0.45% hydrogen peroxide in PBS for 15 minutes and rinsed again. Immunohistochemistry was performed using standard procedures (ABC-Elite, Vector Laboratories, Burlingame, Calif., USA). Briefly, slides were pre-incubated with normal goat serum and blocking avidin for 20 minutes then rinsed in PBS. Monoclonal antibodies were used for detection of alpha-heregulin (Santa Cruz Biotechnology, Santa Cruz, Calif., USA), and the EGF receptor (BD Biosciences, San Diego, USA) at a 1:100 dilution. Slides were incubated with the heregulin antibody and biotin in normal goat serum or with the EGF receptor antibody and biotin in normal horse serum for one hour and rinsed in PBS. The primary antibodies were not included in negative control experiments. Slides were incubated with the secondary antibody (biotinylated anti rabbit IgG made in goat diluted 1:350 in normal goat serum or biotinylated anti mouse IgG made in horse diluted 1:50 in normal horse serum, Vector Laboratories, Burlingame, Calif.) for one hour. Solutions A and B (ABC-Elite, Vector Laboratories, Burlingame, Calif., USA) were added simultaneously for 30 minutes. Diaminobenzidine was used as a chromogen and arrays were visualized and photographed using standard light microscopy.

Typical results of such an assay are shown in FIG. 4.

What is claimed is:

1. A method of preparing a tissue microarray comprising die steps of:
    (a) preparing a frozen tissue embedding compound for receipt of one or more non-fixed biological samples by making an array of holes in the frozen tissue embedding compound; and
    (b) introducing the one or more non-fixed biological samples into the array of holes in the frozen tissue embedding compound; so that the tissue microarray is prepared.

2. The method of claim 1, wherein the array of holes in the frozen tissue embedding compound are made with a needle.

3. The method of claim 1, wherein the method comprises introducing at least two or more non fixed biological samples into the array of holes frozen tissue embedding compound.

4. The method of claim 1, wherein the tissue embedding compound comprises about 10% polyvinyl alcohol and about 4% polyethylene glycol.

5. The method of claim 1, wherein the one or more non-fixed biological samples is fixed after being embedded in the frozen tissue embedding compound.

6. The method of claim 1, further comprising the step of slicing an about 4 µm section off of die frozen tissue embedding compound; wherein the section comprises a portion of the embedded one or more non-fixed biological sample.

* * * * *

UNITED STATES PATENT AND TRADEMARK OFFICE
CERTIFICATE OF CORRECTION

PATENT NO.    : 6,696,271 B2
DATED         : February 24, 2004
INVENTOR(S)   : Dennis J. Slamon and Marlena S. Fejzo It is certified that error appears in the above-identified patent and that said Letters Patent is hereby corrected as shown below:

<u>Title page,</u>
Item [56], References Cited, OTHER PUBLICATIONS, insert -- Axel Hoos et al., "Tissue Microarray Profiling of Cancer Specimens and Cell lines: Opportunities and Limitations," October 2001, Laboratory Investigation, 81(10): 1331-1338 --.

<u>Column 14,</u>
Lines 6 and 28, "die" should read -- the --.
Line 31, "sample" should read -- samples --.

Signed and Sealed this

Twenty-ninth Day of June, 2004

JON W. DUDAS
*Acting Director of the United States Patent and Trademark Office*